(12) United States Patent
Brahmbhatt

(10) Patent No.: US 7,985,574 B2
(45) Date of Patent: Jul. 26, 2011

(54) OXYGEN-ASSISTED FERMENTATION PROCESS

(75) Inventor: Sudhir R. Brahmbhatt, Glencoe, MO (US)

(73) Assignee: American Air Liquide, Inc., Fremont, CA (US)

( * ) Notice: Subject to any disclaimer, the term of this patent is extended or adjusted under 35 U.S.C. 154(b) by 1516 days.

(21) Appl. No.: 10/779,828

(22) Filed: Feb. 17, 2004

(65) Prior Publication Data

US 2005/0181499 A1   Aug. 18, 2005

(51) Int. Cl.
| C12N 1/00 | (2006.01) |
| C12N 1/12 | (2006.01) |
| C12N 1/20 | (2006.01) |
| C12N 5/00 | (2006.01) |
| C12M 1/00 | (2006.01) |
| C12M 1/20 | (2006.01) |

(52) U.S. Cl. .................. 435/243; 435/252.1; 435/283.1; 435/287.1; 435/287.5; 435/813; 435/818

(58) Field of Classification Search .................... 435/243
See application file for complete search history.

(56) References Cited

U.S. PATENT DOCUMENTS

| 4,169,010 A * | 9/1979 | Marwil .......................... 435/247 |
| 4,426,450 A * | 1/1984 | Donofrio ....................... 435/243 |
| 4,808,534 A | 2/1989 | Schick et al. .................. 435/247 |
| 4,992,370 A * | 2/1991 | Kalina ........................... 435/161 |
| 5,158,890 A * | 10/1992 | Kalina ......................... 435/295.1 |
| 5,198,362 A * | 3/1993 | Forsyth et al. .............. 435/254.1 |
| 5,424,196 A | 6/1995 | Cambiaghi |
| 5,798,254 A * | 8/1998 | Cheng .......................... 435/243 |
| 5,972,661 A * | 10/1999 | Kubera et al. ................ 435/104 |
| 5,985,652 A * | 11/1999 | Cheng ........................ 435/286.6 |
| 6,280,996 B1 | 8/2001 | Cheng |
| 6,482,373 B1 * | 11/2002 | Hannaford et al. ............. 423/47 |
| 6,579,085 B1 * | 6/2003 | Satchell et al. .................... 431/8 |
| 6,692,661 B1 * | 2/2004 | Bedetti ......................... 252/373 |
| 7,718,405 B2 * | 5/2010 | Brahmbhatt .................. 435/104 |
| 2002/0115132 A1 * | 8/2002 | Ho et al. ......................... 435/41 |
| 2003/0080446 A1 * | 5/2003 | Cheng ............................ 261/77 |

FOREIGN PATENT DOCUMENTS

| EP | 0341878 | 4/1989 |
| EP | 1038948 | 3/2000 |
| GB | 1457571 | 1/1974 |

OTHER PUBLICATIONS

Chen, Yinliang et al, J. Chem. Tech. Biotechnol. 67, "Continuous Production of Thrombomodulin from a *Pichia pastoris* Fermentation"., pp. 143-148 (1996).*
International Search Report, (2005).

* cited by examiner

*Primary Examiner* — Deborah K. Ware
(74) *Attorney, Agent, or Firm* — Allen E. White; Christopher J. Cronin

(57) ABSTRACT

A fermentation process uses substantially pure oxygen. The oxygen is the only reactive gas which is injected into a fermentation vessel. The oxygen is moved through the vessel solely by its own pressure. The process can be used with both mechanically-agitated and air-lifted fermenters. The mechanically-agitated fermenter includes an analyzer for measuring oxygen concentration in the exhaust line, and adjusting the flow of fresh oxygen into the vessel accordingly. In the air-lifted fermenter, an analyzer measures the oxygen concentration in the head space of the vessel, and operates valves which either recycle the gas from the head space, or vent that gas to the outside, according to the measured concentration. A stream of nitrogen is periodically injected into the vessel to drive out carbon dioxide and other gases, to control the pH of the fermentation medium. The present invention substantially improves the efficiency of a commercial fermentation process.

2 Claims, 4 Drawing Sheets

OXYGEN-ASSISTED FERMENTATION PROCESS

BACKGROUND OF THE INVENTION

The present invention relates to fermentation processes, and provides a method and apparatus for supporting a fermentation process with the use of substantially pure oxygen.

Fermentation is a process whereby a chemical change is induced by a living organism, or by an enzyme produced by an organism. Normally, such organisms are unicellular plants such as yeast, molds, or fungi. The fermentation reactions can be anaerobic, i.e. with no oxygen added, or aerobic, i.e. oxygen-dependent.

Whether the fermentation process is aerobic or anaerobic depends on the particular microorganisms used for the process, and not necessarily on the final product. The choice of whether to use an aerobic or an anaerobic process often depends on practical considerations. For example, citric acid can be made in either way, but for manufacturing in commercial quantities, it is preferred to use an aerobic method, due to economic factors such as substrate, yield, etc.

Optimum cell growth and product formation depend on the design of the fermentation medium. Care must be taken to provide a sufficient amount of air, required trace elements, and the specific nutritional requirements of the cell. Microorganisms will consume glucose as an energy source in preference to any other carbon compounds. The amount of sugar to be charged into a medium is calculated from the maximum population that a fermenter will support aerobically. Also, assimilable nitrogen must be available. Most cells will use ammonia as readily as amino acids. Consequently, ammonium salts are frequently included in the prepared medium.

The yield of the product being made by the fermentation process is ultimately dependent on cell growth of the microorganisms used. Based on the shape of the growth curve for aerobic fermentation, it turns out that the rate of growth is most critical at the beginning of the fermentation cycle, and it is that portion of the cycle that should be emphasized to maximize yield.

For an aerobic fermentation process, the rate of cell growth is, in turn, dependent on the rate at which oxygen is absorbed into the system. It is an aim of the present invention to enhance such absorption of oxygen.

Many valuable chemicals, food, beverages, pharmaceuticals, and farm products are produced by aerobic fermentation. To meet an increasing demand for the final product, the productivity of the process is boosted by a high-strength broth requiring an enhanced oxygen supply. Oxygen demand is highest during the phase of the fermentation process in which the cells are growing exponentially. In this phase, extensive primary metabolism creates a very high oxygen demand, which must be met in order to stimulate cell growth. High viscosity in this phase inhibits oxygen transfer, resulting in oxygen-starved conditions and lower yield.

There are two major kinds of fermentation systems. A mechanically-agitated fermenter comprises a vessel having a mechanical device for agitating the contents of the vessel. Typically, the mechanical device includes a shaft having multiple impeller blades. An air-lifted fermenter does not use a mechanical agitator, but instead relies only on bubbles of air, passing through the contents of the vessel, both to maximize oxygen transfer and to agitate the contents.

A product of the fermentation process is carbon dioxide. Unless vented to the outside, the carbon dioxide forms carbonic acid, which will kill the microorganisms used in the fermentation process. Thus, a practical commercial fermentation process must include means for removing carbon dioxide.

Air contains about 21% oxygen, with the balance being about 78% nitrogen and about 1% other gases. When air is used as the sole source of oxygen in a fermentation process, movement of the air can be used to remove the carbon dioxide. Due to the low concentration of oxygen in ordinary air, most of the oxygen available from the air remains undissolved and vents from the fermenter to the atmosphere. An aerobic fermentation process works with dissolved oxygen; any oxygen that is not dissolved will not affect the process. The venting of undissolved air makes it difficult to obtain even the minimal desired level of dissolved oxygen, required to sustain the microorganism growth needed to achieve desired production levels.

A common solution to the above problem with air-based fermentation systems is to increase the air flow. But this technique is helpful only when the oxygen demand is moderate. If the reaction has a high rate of oxygen uptake, an increased flow of air tends to flood the impellers in a mechanically-agitated fermenter. In an air-lifted fermenter, an increased flow of air can fluidize the entire contents of the vessel, and can blow the contents out of the fermenter.

Installing larger agitators and motors may improve the oxygen transfer rate in the fermentation vessel, but doing so is expensive. Even if the capital expenditure is of no concern, large agitators and more powerful motors can provide only incremental improvements in the oxygen transfer rate.

Another possible solution to the problem of increasing the amount of oxygen delivered to a fermentation process is to use oxygen-enriched air. The enriched air can be created by adding pure oxygen to a stream of ordinary air before it enters the vessel. Due to the fire hazard associated with the use of oxygen, care must be taken to be sure that oxygen does not flow back into the air conduit. Also, care must be taken to prevent oil from leaking from the air compressor, so as to prevent such oil from coming into contact with the oxygen.

Because enriched air is distributed to the contents of the vessel using the same sparger that would be used with ordinary air, the dissolution efficiency of enriched air is just as poor as that of ordinary air. Moreover, the use of pure oxygen in addition to ordinary air adds to the cost of the system, because one must manage two separate supply sources. Thus, the use of enriched air in a fermentation system is only marginally economical, and of only limited benefit.

The present invention solves the above problems, by providing a system and method in which substantially pure oxygen is safely injected into a fermentation vessel. The present invention provides an improved fermentation process and apparatus, having substantially improved efficiency, and in which the cost of operation is greatly reduced.

SUMMARY OF THE INVENTION

The present invention comprises a fermentation process and apparatus, wherein substantially pure oxygen is directed into the fermentation medium.

In its most basic form, the process comprises directing substantially pure oxygen into a fermentation vessel, such that the pure oxygen is the only reactive gas injected into the vessel from an external source. In the case of a mechanically-agitated fermenter, the oxygen is the only gas, external to the vessel, that is directed into the vessel. In the case of an air-lifted fermenter, there may be an additional stream of nitrogen, or other inert gas, which is periodically introduced for the purpose of carrying away carbon dioxide and other undesirable products of the fermentation process. In both cases, there is no blower or compressor, or the like, to move the oxygen through the system. Instead, the movement of oxygen through the vessel is due only to the pressure of the oxygen in the oxygen supply.

When the process of the invention is practiced with a mechanically-agitated fermenter, the contents of the vessel are agitated by a mechanical device, as the oxygen is directed into the vessel. An oxygen analyzer monitors the concentration of oxygen in the exhaust from the vessel, and adjusts a valve to control the flow of fresh oxygen from the oxygen supply. In this way, the concentration of oxygen in the exhaust is maintained at a level that is comparable to the concentration of oxygen in ordinary air. Also, carbon dioxide readily flows out of the system through an exhaust vent.

In the case of an air-lifted fermenter, the oxygen is again directed into the vessel, but preferably with a diffuser that directs the oxygen to various locations throughout the volume of the vessel. An oxygen analyzer continuously measures the concentration of oxygen in the head space in the vessel. If the concentration is larger than a desired set point, the analyzer opens a valve that causes gas from the head space to be re-directed into the vessel. If the concentration is smaller than the desired set point, the analyzer opens an exhaust valve that allows gas from the head space to vent to the outside. The concentration of oxygen in the exhaust is preferably maintained at or below the concentration of oxygen in ordinary air.

A pH control unit monitors the pH of the fermentation medium. When the pH falls to a predetermined set point, implying that there is too much carbon dioxide in the medium, the control unit operates a valve to allow nitrogen, or another relatively inert gas, to flow through the vessel, carrying the carbon dioxide, and other undesirable gases formed by the fermentation process, out of the fermentation medium and into the head space. The carbon dioxide and nitrogen are then vented from the head space, due to the fact that an accumulation of carbon dioxide reduces the concentration of oxygen in the head space, and thereby causes the exhaust valve to open automatically.

The invention also includes the apparatus used for performing the method described above.

The present invention therefore has the primary object of providing an improved process and apparatus for fermentation.

The invention has the further object of providing a fermentation process in which substantially pure oxygen is used to drive the process, and in which the hazards associated with the use of pure oxygen are greatly reduced.

The invention has the further object of providing a fermentation process using substantially pure oxygen, wherein the process can be practiced with existing fermentation equipment, with minimal modification.

The invention has the further object of providing a fermentation process using substantially pure oxygen, wherein the oxygen is the only gas, external to the fermentation vessel, that is injected into the fermenter.

The invention has the further object of providing a fermentation process and apparatus, wherein the sole means for conveying oxygen through the system is the pressure of the oxygen itself.

The invention has the further object of improving the efficiency of a fermentation process, by improving the yield of such process while reducing the costs associated therewith.

The invention has the further object of providing an air-lifted fermenter which automatically removes excess carbon dioxide from the system.

The reader skilled in the art will recognize other objects and advantages of the present invention, from a reading of the following brief description of the drawings, the detailed description of the invention, and the appended claims.

DETAILED DESCRIPTION OF THE INVENTION

The present invention is based on the discovery that the use of pure oxygen, injected into a fermentation vessel by a proper injection technique, significantly improves the oxygen utilization of the fermentation process, while maintaining a high level of safety. The direct injection of oxygen provides for safe, controlled dissolution of high-purity oxygen in the fermenter. In the present invention, the stream of pure oxygen is the only reactive gas, from an external source, that is injected into the vessel.

For a typical fermentation cycle, oxygen demand is relatively low at the beginning of the process. After a certain lag time, the growth of microorganisms becomes exponential, and the oxygen demand increases rapidly. Direct injection of oxygen at this point permits a significant increase in oxygen dissolution in the fermentation medium, and avoids oxygen starvation, and enhances the efficiency of the process. When pure oxygen is dissolved in the medium, the concentration of oxygen in the medium is five times greater than the concentration would be if ordinary air were used instead of pure oxygen. The use of pure oxygen also increases the rate of oxygen dissolution. And, as noted above, it is only dissolved oxygen that affects the fermentation process. Later in the cycle, the growth of the biomass in the fermenter reaches a stationary phase, and the demand for oxygen is reduced.

The efficiency of the fermentation process is directly related to the oxygen utilization efficiency, which is the amount of oxygen dissolved per unit of oxygen injected into the fermenter. With the present invention, the yield of a fermentation process can be increased by up to 65%, as compared with processes of the prior art.

Figure 1:
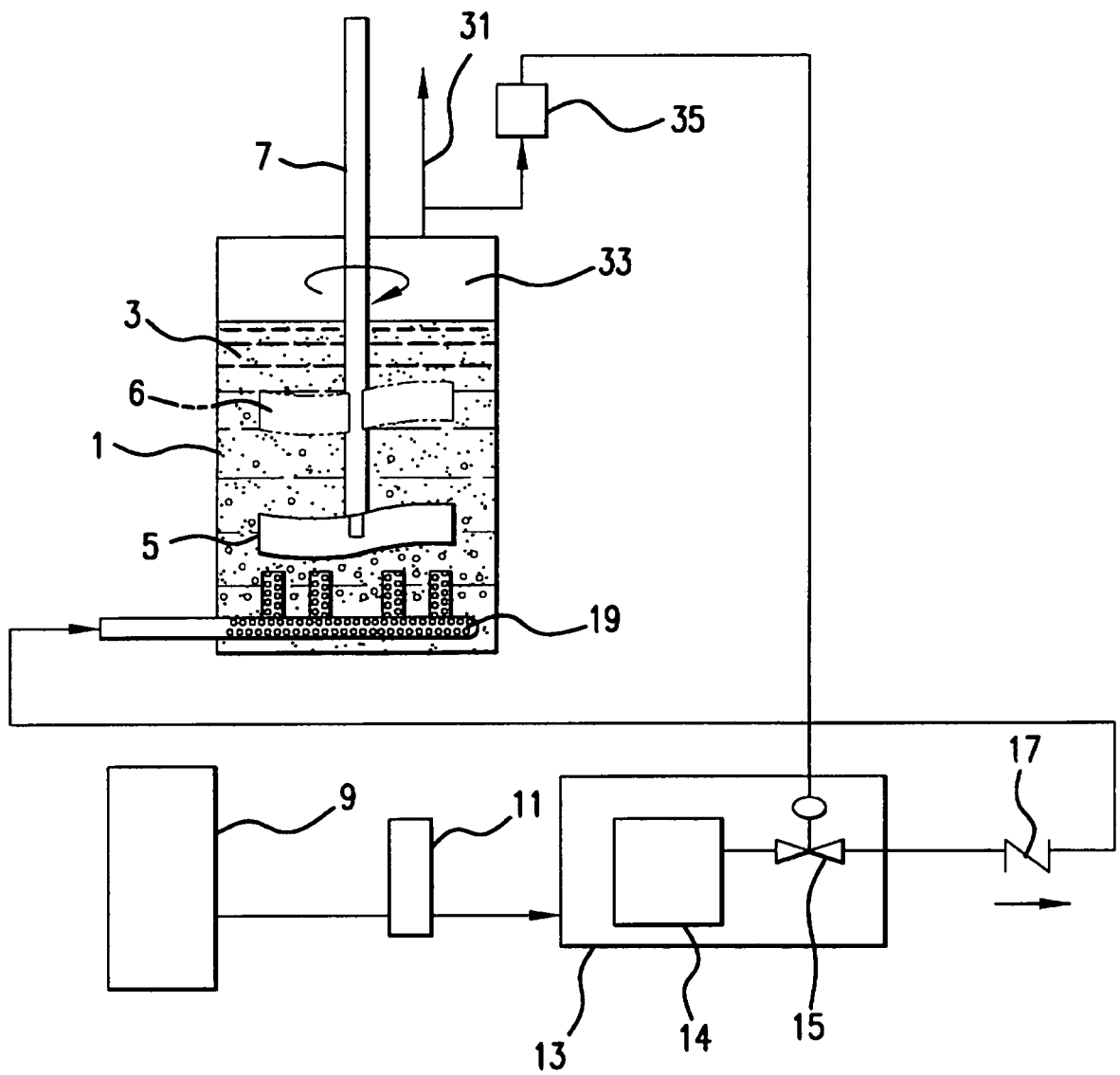
FIG. 1 provides a schematic diagram of one preferred embodiment of the present invention, in which the fermentation is conducted in a mechanically-agitated fermenter.

FIG. 1 provides a schematic diagram of one preferred embodiment of the present invention. This embodiment uses a mechanically-agitated fermenter. The fermenter is defined by vessel 1 which contains fermentation medium 3. The contents of the vessel are agitated by one or more impellers or agitators 5 and 6 connected to rotatable shaft 7. For simplicity of illustration, the motor or other means for rotating the shaft is not shown.

It has been found that, due to its use of substantially pure oxygen, a mechanically-agitated fermenter of the present invention requires the use of only one impeller. The impeller has the effect of shearing the oxygen bubbles as they leave a diffuser located near the impeller. This shearing causes the bubbles to become more finely divided, so that the bubbles more readily dissolve into the medium. Moreover, the use of pure oxygen, instead of air, further enhances the dissolution of oxygen, because there is little or no nitrogen to interfere with the dissolution process. For these reasons, the present invention does not require quite the same amount of mechanically induced turbulence as required by the prior art.

Many existing mechanically-agitated fermenters, however, have two or more impellers, usually spaced at different vertical positions. The present invention can be used with such systems, and it is not necessary to change the number of impellers. If only one impeller is used, it should be located near the bottom of the vessel, preferably about 10-12 inches from the bottom. An advantage of using only one impeller is the reduction of the mechanical load, which reduces energy costs. In FIG. 1, impeller 6 is shown in dotted outline to symbolize the fact that this impeller is optional. Impeller 5 represents the impeller that is normally present in all systems using mechanical agitation.

A stream of substantially pure oxygen is injected into the fermentation vessel 1. The oxygen originates from oxygen supply 9. The oxygen supply could be a tank containing liquid or gaseous oxygen. If the oxygen is stored in liquid form, a vaporization unit 11 is used to convert the oxygen to a gas. Alternatively, the oxygen could be stored as a compressed gas, or it could be continuously generated at the site, such as by an air-separation membrane system or pressure swing adsorption (PSA) unit, in which case the vaporization unit would be omitted.

Gaseous oxygen then passes through oxygen control unit 13, which includes a control panel 14. The oxygen leaves unit 13 through mechanically adjustable oxygen flow control valve 15 and check valve 17, and flows into the vessel through diffuser 19.

Figure 3:
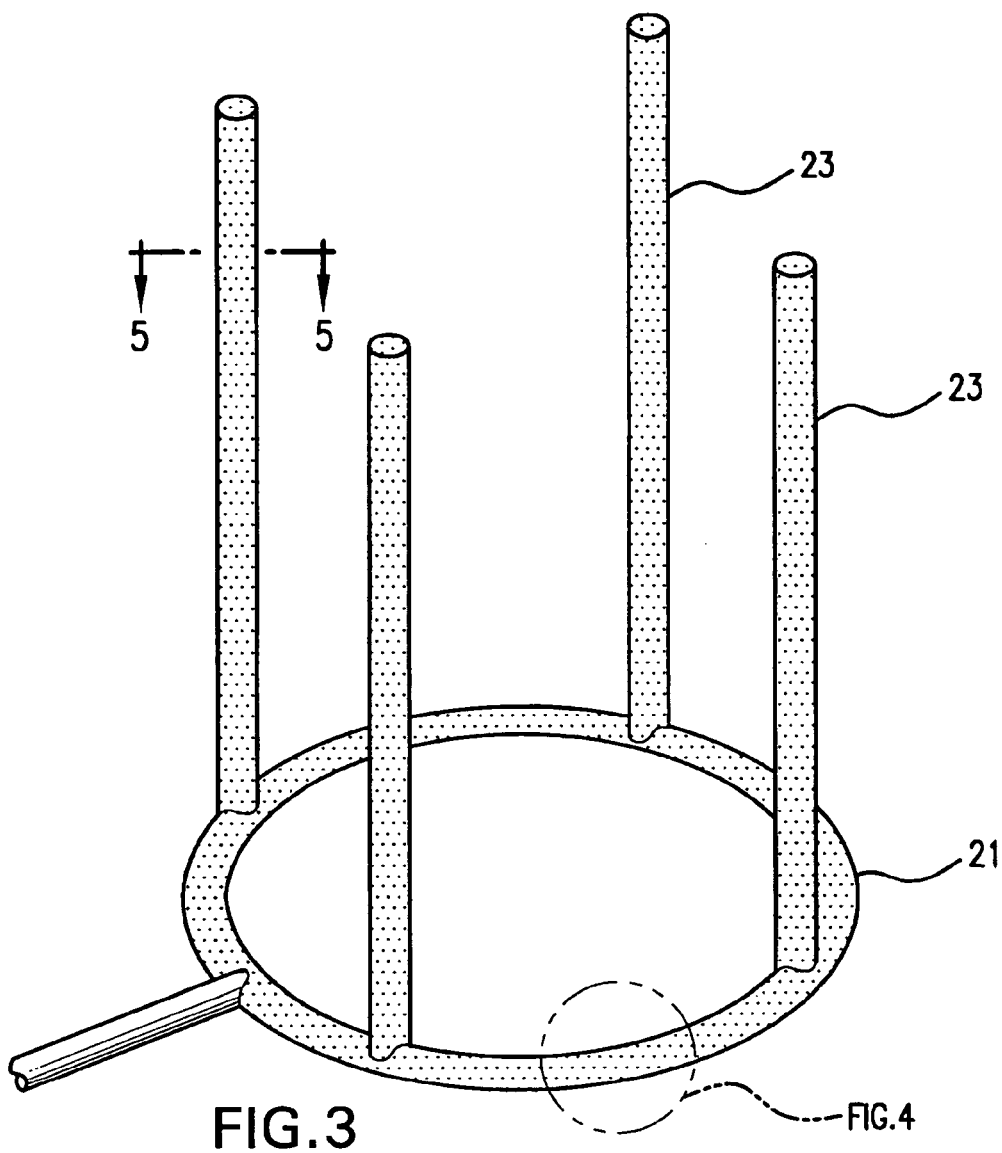
FIG. 3 provides a perspective view of a portion of a diffuser used in the present invention to disperse bubbles of air through the contents of a fermentation vessel.
Figure 4:
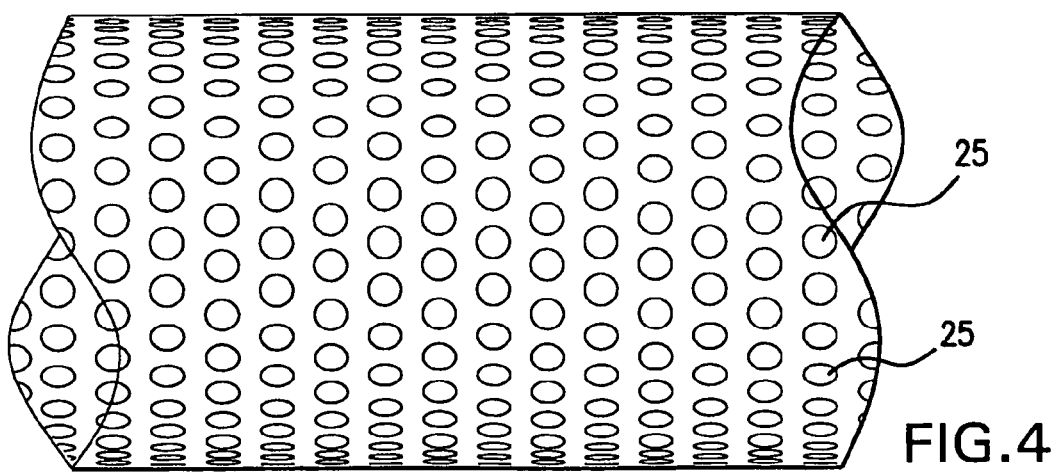
FIG. 4 provides a side elevational view of a portion of a pipe used to make the diffuser of the present invention, showing rows of holes along its periphery to allow oxygen gas to escape.
Figure 5:
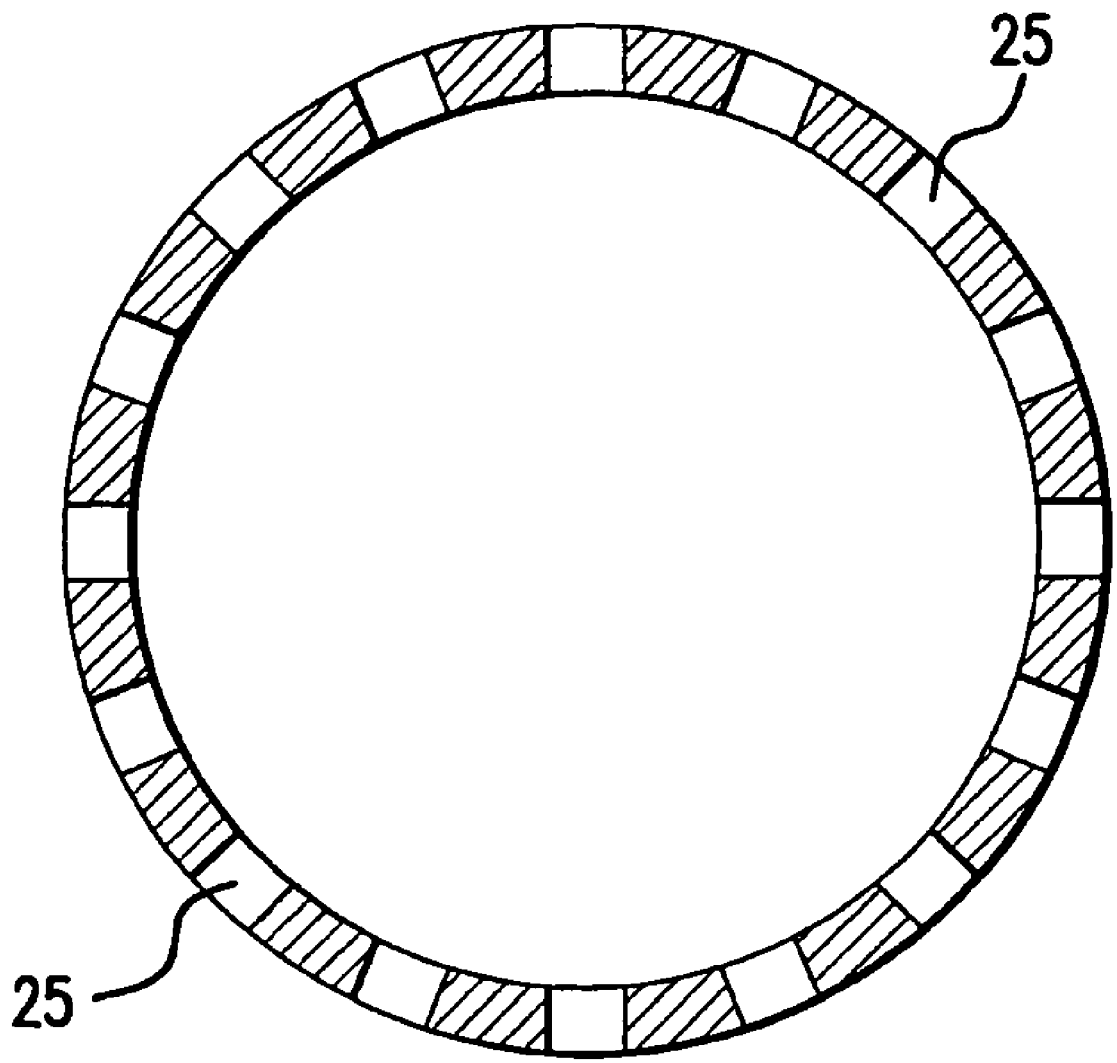
FIG. 5 provides a cross-sectional view of a portion of the pipe used to make the diffuser of the present invention, showing the locations of the holes disposed around its periphery.

The structure of diffuser 19 is illustrated in FIGS. 3-5. In the preferred embodiment, the diffuser includes a generally circular, perforated pipe 21, oriented near the bottom of the vessel, and defining a plane that is approximately parallel to that of the bottom. A plurality of vertical members 23 extend from the circular pipe, each vertical member similarly comprising a perforated pipe, as shown in FIG. 3.

FIG. 4 provides a side elevational view of a portion of the pipe used to construct the diffuser, and shows rows of perforations 25 disposed along the periphery of the pipe. FIG. 5 illustrates the pipe in a cross-sectional view, showing that the perforations allow fluid flow from the inside of the pipe to the outside.

The perforations 25 in the pipe are shown in generally diagonal rows. This arrangement creates a swirling effect as the oxygen bubbles pass through the pipe. The swirling effect creates more turbulence, and achieves better mixing of the oxygen with the contents of the vessel.

In the mechanically-agitated fermenter shown in FIG. 1, the vertical members are relatively short, and do not quite extend up to the vertical position of the lower impeller 5. By introducing the oxygen bubbles near the level of the impeller, or the lowest of several impellers, the bubbles are most likely to be sheared off by the action of the impeller, so that they become even more finely divided. By making small bubbles even smaller, the impeller further enhances the dissolution of the oxygen in the medium. For a mechanically-agitated system, it is therefore not necessary to dispense oxygen throughout the vessel, because the oxygen becomes fully diffused by action of the impeller(s).

In the preferred embodiment, the holes in the diffuser should be small and numerous. For example, the holes may have a diameter of $\frac{1}{16}$ or $\frac{1}{8}$ inches. These sizes are generally smaller than those used with diffusers of the prior art. However, the invention should not be deemed limited by the choice of the size of the holes. Small holes are desirable because small holes produce small bubbles, which are easier to dissolve than large bubbles. As noted already, if the oxygen does not dissolve in the medium, it cannot support the fermentation process.

Exhaust vent 31 directs gases from head space 33 of vessel 1 to the outside environment. The exhaust vent is connected to oxygen analyzer 35, which determines the concentration of oxygen in the exhaust gas. If the concentration of oxygen is greater than desired, the analyzer sends a signal to adjustable oxygen flow control valve 15, changing the setting of the valve so as to reduce the flow of oxygen into the vessel. If the concentration of oxygen is less than desired, the analyzer sends a signal to valve 15 so as to increase the flow of oxygen into the vessel. In the preferred embodiment, the analyzer 35 is programmed to maintain the concentration of oxygen, in the head space 33, at about the same level as is found in ordinary air. Thus, there is no danger of an explosion due to oxygen, as the exhaust has no greater concentration of oxygen than is found in ordinary air. Note also that the measurement of oxygen concentration in the exhaust, and the control of the flow of fresh oxygen into the vessel, are preferably performed substantially continuously.

A key byproduct of the fermentation process is carbon dioxide. As noted above, the carbon dioxide forms carbonic acid, which tends to kill the microorganisms in the fermenter. Thus, it is necessary to remove the carbon dioxide. A preferred means of doing so is by inducing turbulence in the vessel. In the mechanically-agitated fermenter shown in FIG. 1, the turbulence is produced by the impeller(s). This function of the impeller is in addition to its other functions, namely that of mixing the oxygen with the contents of the vessel, and of shearing the oxygen bubbles to make them more readily dissolve into the fermentation medium.

Figure 2:
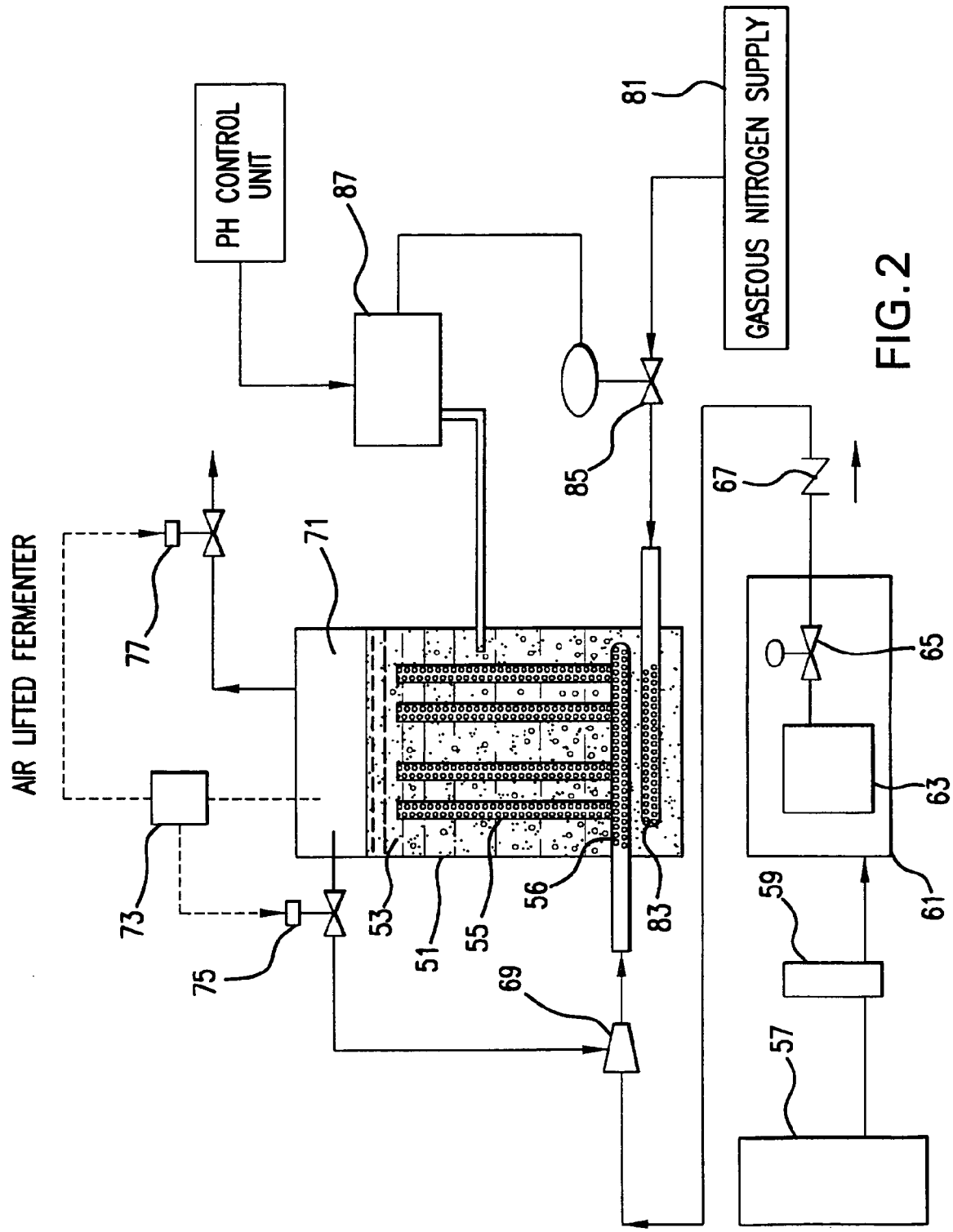
FIG. 2 provides a schematic diagram of another preferred embodiment of the present invention, in which the fermentation is conducted in an air-lifted fermenter.

FIG. 2 provides a schematic diagram of another preferred embodiment of the present invention, in which the fermenter is air-lifted. In an air-lifted fermenter, the turbulence needed to mix the oxygen with the contents of the vessel is provided by the movement of the oxygen bubbles themselves, and there is no separate impeller or other motion-producing device within the vessel.

As shown in FIG. 2, the fermenter includes vessel 51 that holds fermentation medium 53. As in the embodiment of FIG. 1, there is a diffuser 55, preferably having a structure similar to what is shown in FIGS. 3-5, except that its vertical members are taller, and extend along the majority of the vertical dimension of the vessel, as shown in FIG. 2. Thus, oxygen is released at many locations within the vessel, so as to mix thoroughly with the fermentation medium, and also so as to induce the necessary turbulence within the medium.

Oxygen is taken from supply 57. The oxygen, if in liquid form, is vaporized in vaporizer 59. As in the other embodiment, the vaporizer would be omitted if the oxygen were stored as a compressed gas, or produced locally by a membrane or PSA system. Gaseous oxygen flows into oxygen control unit 61, which includes control panel 63. Oxygen flowing out of the control unit passes through flow control valve 65, and check valve 67. The oxygen is then directed into eductor 69, which directs the oxygen into the diffuser 55.

One difference between a mechanically-agitated and an air-lifted fermenter is that mechanical agitation is usually more effective in mixing the oxygen with the contents of the vessel, and in enhancing the dissolution of oxygen in the fermentation medium. Thus, in the air-lifted fermenter, there is likely to be a larger amount of pure oxygen appearing in the head space. This oxygen represents not only a potential safety problem, but also constitutes an economic waste, insofar as the oxygen in the head space has not reacted with the contents of the vessel. Therefore, the air-lifted fermenter is provided with recycling means for returning unreacted oxygen to the vessel, and for controlling the oxygen concentration in the exhaust.

Oxygen analyzer 73 is connected to a probe extending into the head space 71, and measures the oxygen concentration in that space. The block which shows the analyzer is intended also to symbolize a transducer, or converter, which converts a pressure reading into an electric current. The electric current is then used to control the setting of normally-closed valve 75 and exhaust valve 77. Note that the analyzer could itself produce an output that is either a pressure or an electric current, and that many different arrangements could be used in the position of the block labeled by reference numeral 73.

When the oxygen concentration in the head space rises above a predetermined set point, the analyzer 73 is programmed to open the valve 75, thereby directing gas from the head space towards the eductor 69. An eductor is used to draw fluid into the valve, so that the fluid can be conveyed into the vessel. The unused oxygen in the head space is therefore not vented to the outside, but is recirculated to the vessel, so that it can again be exposed to the fermentation medium.

When the oxygen concentration in the head space falls below the predetermined set point, the analyzer causes exhaust valve 77 to open, while keeping valve 75 closed. Thus, the gas in the head space vents to the atmosphere.

Since some of the gas in the head space will be carbon dioxide, in addition to oxygen and various organic gases, recycling of the head space gas causes carbon dioxide gas to be recycled along with the oxygen and other organic gases. Recycling of carbon dioxide has the undesirable effect of decreasing the pH of the medium, and thus harming the growth of organisms needed for the fermentation process.

The embodiment of FIG. 2 includes apparatus to overcome the problem of too much carbon dioxide in the medium. Control unit 87 continuously monitors the pH of the fermentation medium, and operates valve 85 to control the flow of gaseous nitrogen from nitrogen supply 81. Instead of nitrogen, one could use some other inert, or relatively inert, gas. When the concentration of carbon dioxide is sufficiently high to reduce the pH below a predetermined set point, the valve 85 is opened, and nitrogen gas enters the vessel 51 through nitrogen diffuser 83. The nitrogen diffuser creates relatively large bubbles of nitrogen, which carry the carbon dioxide gas, and other undesirable organic gases formed in the fermentation process, out of the fermentation medium and into the head space. This flow of carbon dioxide into the head space causes the oxygen concentration in the head space to drop. Eventually, the drop in oxygen concentration of the head space gas will cause the exhaust valve to open, as described above, thereby allowing the carbon dioxide to vent to the outside.

The nitrogen diffuser 83 may be constructed in a manner similar to that of the oxygen diffuser. However, in general, the holes in the nitrogen diffuser are preferably larger than the corresponding holes of the oxygen diffuser. In one example, the holes in the nitrogen diffuser may have a diameter in the range of about 0.125-0.250 inch. This example is not intended to limit the invention. The larger holes create the larger bubbles needed to carry the carbon dioxide gas out of the medium.

Also, the nitrogen diffuser does not include the vertical portions used for the oxygen diffuser. If the nitrogen diffuser is made of a generally circular section of pipe, the circular section should have a diameter different from that of the corresponding part of the oxygen diffuser, so that one diffuser does not obstruct the other. In FIG. 2, the diameter of the nitrogen diffuser 83 is shown to be somewhat less than that of the oxygen diffuser above it.

The pH of the fermentation medium is preferably held at a level that does not interfere with the organisms that are responsible for the fermentation process. The use of nitrogen is automatically optimized, because the nitrogen is supplied only when needed to adjust the pH of the medium.

The use of nitrogen in the air-lifted fermenter is not likely to increase the cost of the system significantly. Most fermentation facilities already use nitrogen for other purposes. Therefore, nitrogen is usually available for the purpose described above.

Because an air-lifted fermenter does not achieve optimum mixing on the first passage of oxygen through the vessel, the concentration of oxygen in the head space will be greater than the concentration of oxygen in the head space of a mechanically-agitated fermenter, but still less than the concentration of oxygen in ordinary air. For this reason, as explained above, when using an air-lifted fermenter, it is preferable to recycle the oxygen from the head space back into the vessel, and to maintain the concentration of oxygen in the head space at a predetermined level. In one preferred embodiment, the predetermined set point may be 6% or 8% oxygen, or some other figure that is substantially less than 21%. Operating in this manner further reduces the likelihood of an explosion due to the handling of pure oxygen.

In both the mechanically-agitated fermenter and the air-lifted fermenter of the present invention, the stream of substantially pure oxygen is the only gas, from any external source, that directly participates in the fermentation process. Except for the nitrogen used to carry away carbon dioxide, in the case of the air-lifted fermenter, there is no gas originating from outside of the vessel, that is ever conveyed into the vessel. In both cases, there is no ambient air, from outside the vessel, that is ever conveyed into the vessel. In the case of the mechanically-agitated fermenter, the only gaseous input to the vessel comes from the oxygen supply. In the case of the air-lifted fermenter, the gaseous input to the vessel comes either from the oxygen supply or from gas recycled from the head space, or from the nitrogen used to remove carbon dioxide. The recycled gas from the head space is not considered to come from any external source.

In both the mechanically-agitated and air-lifted fermenters shown in FIGS. 1 and 2, the vertical members of the diffuser have a structure which is equivalent to that of vertical members 23 shown in FIG. 3, except that the height of each vertical member is greater in the embodiment of FIG. 2.

It is an important feature of the present invention that there is no compressor and no air line. Oxygen flows through the system due only to the pressure of the oxygen supply. The absence of a compressor not only reduces the cost of operation, but eliminates a potential hazard, since there is no heated oil that might react explosively with oxygen. Also, the absence of an air line not only reduces the complexity, and therefore the cost, of the system, but also eliminates the problem of back flow of oxygen into an air line. In the prior art, air and oxygen have been injected through separate fluid lines into a fermentation vessel. In the present invention, there is only one oxygen-containing gas stream injected into the vessel from an external source.

An important feature of the present invention is that it can be very easily adapted for use with existing equipment. The invention can be used with virtually any existing mechanically-agitated or air-lifted fermenter, and thus can be practiced without a large capital expenditure.

The invention may be practiced in either a continuous or batch fermentation process.

The fermentation process of the present invention has been shown to reduce energy consumption by up to 35%, in a mechanically-agitated, continuously operated fermenter, while achieving a production increase of from 20-50%, based on the measured residual sugar (RS) level. The oxygen utilization has been measured at 70-100% of the input.

In a batch fermenter, the present invention has been shown to achieve a significant reduction of cycle time, from about 24-30 hours to about 13-17 hours. This result directly translates into an increase in production. The batch fermenter also experienced reductions in energy usage, and increases in oxygen utilization, comparable to what was experienced with the continuous fermenter.

The invention can be modified in various ways. For example, the exact configuration of the diffuser can be changed, and is not limited to the ring structure shown in the drawings. The configuration of the holes on the pipes defining the diffuser can also be modified. These and other modifications, which will be apparent to those skilled in the art, should be considered within the spirit and scope of the following claims.

What is claimed is:

1. In a fermentation process, the process including the steps of placing a fermentation medium in a vessel, maintaining the fermentation medium in the vessel for a sufficient time to enable a fermentation process to occur in the vessel, and withdrawing a product from the vessel, The improvement comprising injecting a stream of substantially pure oxygen into the vessel while the fermentation process is occurring, wherein the stream of substantially pure oxygen is the sole reactive gas, from any source external to the vessel that is injected into the vessel, and wherein the stream of substantially pure oxygen is the only gas that is injected continuously into the vessel, and wherein the stream of substantially pure oxygen is moved through the vessel solely due to pressure in an oxygen supply and wherein the process is performed without mechanical agitation of contents of the vessel, and wherein the process includes measuring a concentration of oxygen in a head space in the vessel, recycling gas from the head space into the vessel if the concentration of oxygen is greater than a predetermined level, and venting gas from the head space to a region outside the vessel if the concentration of oxygen is less than a predetermined level.

2. The improvement of claim 1, wherein the measuring step is performed substantially continuously.

* * * * *